United States Patent
Di Carlo et al.

(10) Patent No.: US 9,522,344 B2
(45) Date of Patent: Dec. 20, 2016

(54) METHOD AND DEVICE FOR HIGH-THROUGHPUT SOLUTION EXCHANGE FOR CELL AND PARTICLE SUSPENSION

(75) Inventors: Dino Di Carlo, Los Angeles, CA (US); Daniel R. Gossett, Los Angeles, CA (US); Henry T. K. Tse, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 578 days.

(21) Appl. No.: 13/884,595

(22) PCT Filed: Nov. 14, 2011

(86) PCT No.: PCT/US2011/060536
§ 371 (c)(1),
(2), (4) Date: May 9, 2013

(87) PCT Pub. No.: WO2012/067985
PCT Pub. Date: May 24, 2012

(65) Prior Publication Data
US 2013/0228530 A1 Sep. 5, 2013

Related U.S. Application Data

(60) Provisional application No. 61/415,067, filed on Nov. 18, 2010.

(51) Int. Cl.
*B01D 12/00* (2006.01)
*B01L 3/00* (2006.01)
*G01N 15/14* (2006.01)

(52) U.S. Cl.
CPC ......... *B01D 12/00* (2013.01); *B01L 3/502761* (2013.01); *B01L 3/502776* (2013.01);
(Continued)

(58) Field of Classification Search
CPC ................. B01D 11/0496; B01D 12/00; B01L 3/502761; B01L 3/502776; B01L 3/502746; B01L 2200/0652; B01L 2400/0487; B01L 2400/084; B01L 2300/0816; G01N 35/00; G01N 15/06; G01N 33/48; G01N 33/533; G01N 33/52; G01N 2015/149
See application file for complete search history.

(56) References Cited

U.S. PATENT DOCUMENTS 6,432,630 B1 * 8/2002 Blankenstein ......... B01D 57/02
422/186
7,745,207 B2 6/2010 Jovanovich et al.
(Continued)

FOREIGN PATENT DOCUMENTS

WO 2004/025266 A2 3/2004
WO 2006/037561 A1 4/2006
WO 2008/130977 A2 10/2008

OTHER PUBLICATIONS

Zhang et al. Continuous flow separation of particles within an asymmetric microfluidic device, 2006, RSC, Lap Chip, 6, 561-566.*
(Continued)

*Primary Examiner* — David C Mellon
(74) *Attorney, Agent, or Firm* — Vista IP Law Group LLP

(57) ABSTRACT

A method of exchanging fluids with suspended particles includes providing a microfluidic device with a first inlet channel operatively coupled to a source of particles and a second inlet channel operatively coupled to an exchange fluid. A transfer channel is connected at a proximal end to the first inlet channel and the second inlet channel. First and second outlet channels are connected to a distal end of the transfer channel. The source of particles is flowed at a first flow rate into the first inlet channel while the exchange fluid is flowed at a second flow rate into the second inlet channel wherein the ratio of the second flow rate to the first flow rate is at least 1.5. Particles are collected in one of the first and second outlet channels while fluid substantially free of
(Continued)

particles is collected in the other of the first and second outlet channels.

15 Claims, 8 Drawing Sheets

(52) U.S. Cl.
CPC . *B01L 3/502746* (2013.01); *B01L 2200/0652* (2013.01); *B01L 2300/0816* (2013.01); *B01L 2400/0487* (2013.01); *B01L 2400/084* (2013.01); *G01N 2015/149* (2013.01)

(56) References Cited

U.S. PATENT DOCUMENTS

| | | | |
|---|---|---|---|
| 8,361,415 | B2 | 1/2013 | Di Carlo et al. |
| 2003/0159999 | A1 | 8/2003 | Oakey et al. |
| 2008/0124779 | A1 | 5/2008 | Oh et al. |
| 2008/0194012 | A1 | 8/2008 | Lee et al. |
| 2009/0014360 | A1* | 1/2009 | Toner ............... B01D 21/0087 209/208 |
| 2009/0078614 | A1 | 3/2009 | Varghese et al. |
| 2009/0117555 | A1* | 5/2009 | Kuypers ............. G01N 15/147 435/6.14 |
| 2010/0297733 | A1* | 11/2010 | Lin ...................... B03C 1/288 435/239 |

OTHER PUBLICATIONS

Gossett et al., Label-free cell separation and sorting in microfluidic systems, Apr. 25, 2010, Springer, Anal Bioanal Chem, 397, pp. 3249-3267.*
Di Carlo, Inertial microfluidics, Sep. 22, 2009, Royal Society of Chemistry, Lab Chip, 9, pp. 3038-3046.*
DiCarlo et al., Continuous inertial focusing, ordering, and separation of particles in microchannels, Proc. Natl. Acad. Sci. 104(48): 18892-18897 (2007).
Gossett, D. Analytical Chemistry, 2009, 81(20) 8459-8465.
Morton, K.J. et al., Crossing microfluidic streamlines to lyse, label and wash cells, Lab Chip 8, 1448-1453 (2008).
Petersson, F. et al., Carrier Medium Exchange through Ultrasonic Particle Switching in Microfluidic Channels, Anal. Chem. 77, 1216-1221 (2005).
Tornay, R. et al., Dielectrophoresis-based particle exchanger for the manipulation and surface functionalization of particles, Lab Chip 8, 267-273 (2008).
Yamada M. et al., Millisecond treatment of cells using microfluidic devices via two-step carrier medium exchange, Lab Chip, 8, 772-778 (2008).
PCT International Preliminary Report on Patentability (Chapter I of the Patent Cooperation Treaty) for PCT/US2011/060536, Applicant: The Regents of the University of California, Form PCT/IB/326 and 373, dated May 30, 2013 (6pages).
PCT International Search Report for PCT/US2011/060536, Applicant: Boston Scientific Scimed, Inc., Form PCT/ISA/210 and 220, dated May 18, 2012 (5pages).
PCT Written Opinion of the International Search Authority for PCT/US2011/060536, Applicant: Boston Scientific Scimed, Inc., Form PCT/ISA/237, dated May 18, 2012 (4pages).
The extended European Search Report dated Aug. 3, 2016 in European Application No. 11841406.9-1371, Applicant: The Regents of the University of California, (9 pages).
EPO Communication dated Aug. 16, 2016 in European Application No. 11841406.9-1371, Appliant: The Regents of the University of California, (1 page).

* cited by examiner

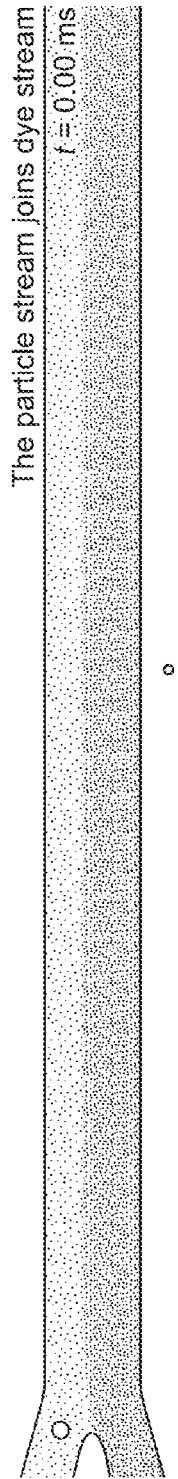

FIG. 2A — The particle stream joins dye stream, $t = 0.00$ ms

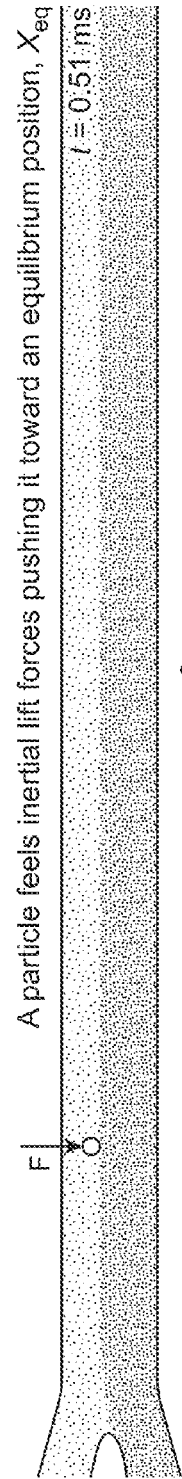

FIG. 2B — A particle feels inertial lift forces pushing it toward an equilibrium position, $X_{eq}$, $t = 0.51$ ms

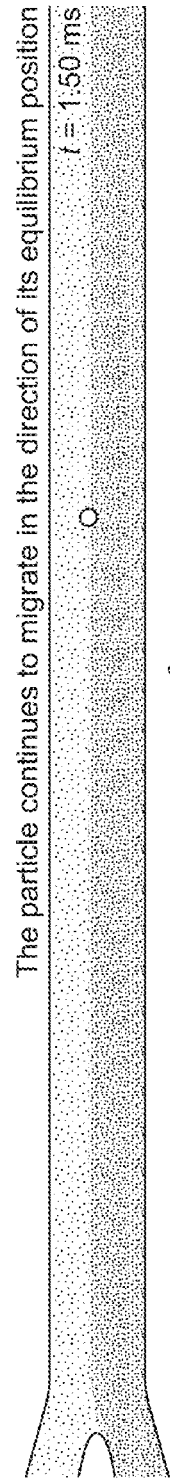

FIG. 2C — The particle continues to migrate in the direction of its equilibrium position, $t = 1.50$ ms

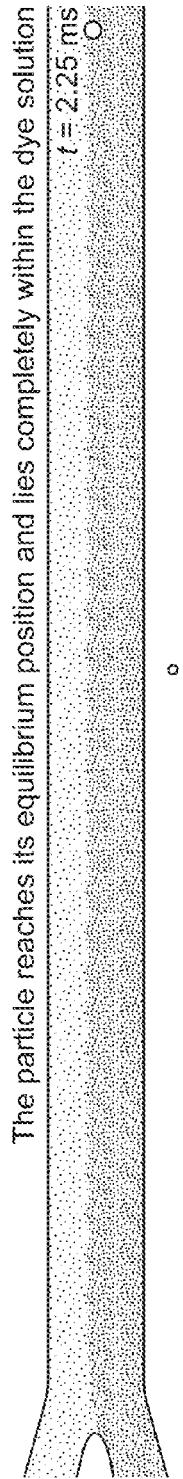

FIG. 2D — The particle reaches its equilibrium position and lies completely within the dye solution, $t = 2.25$ ms Note: Due to the high Peclet number, convection downstream dominates over lateral diffusion

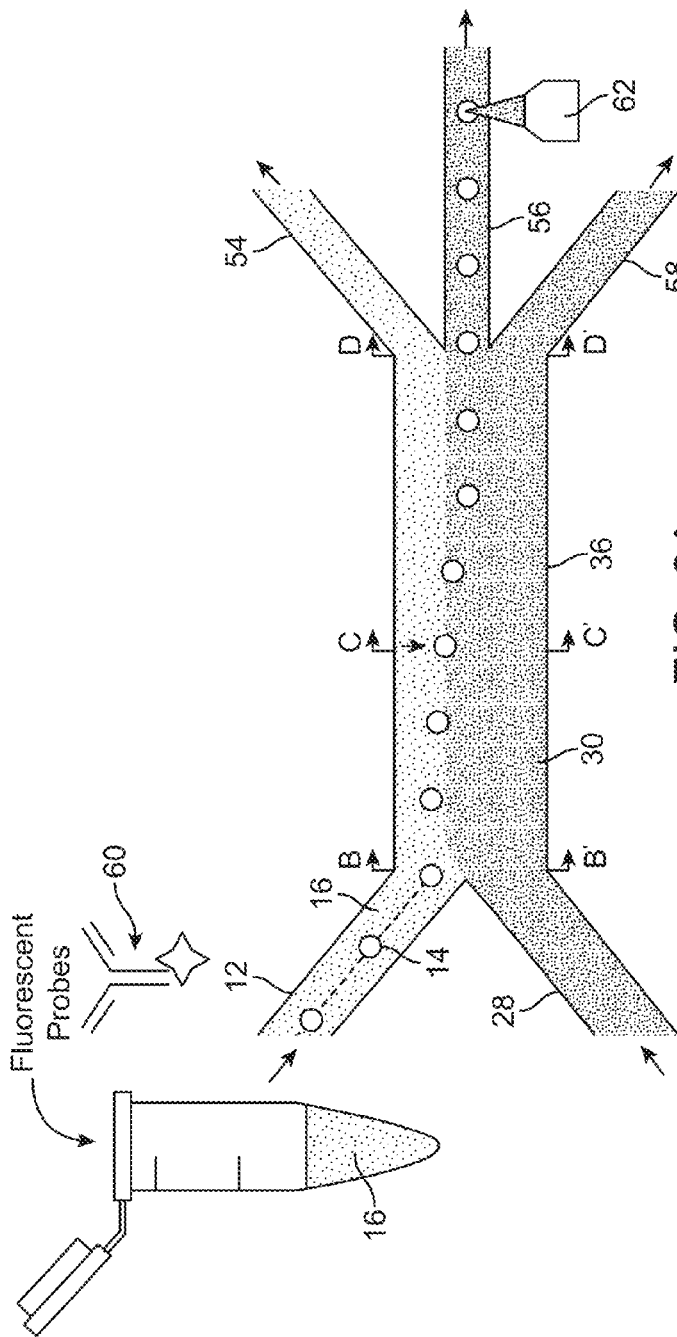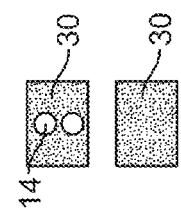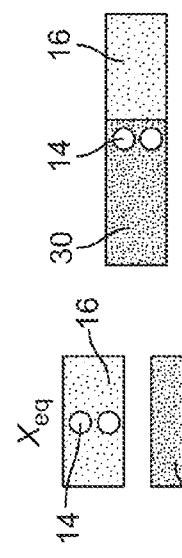

METHOD AND DEVICE FOR HIGH-THROUGHPUT SOLUTION EXCHANGE FOR CELL AND PARTICLE SUSPENSION

RELATED APPLICATION

This Application is a U.S. National Stage filing under 35 U.S.C. §371 of International Application No. PCT/US2011/060536, filed Nov. 14, 2011, which claims priority to U.S. Provisional Patent Application No. 61/415,067 filed on Nov. 18, 2010. The contents of the aforementioned applications are hereby incorporated herein by reference in their entirely. Priority to the aforementioned applications are hereby expressly claimed in accordance with 35 U.S.C. §§119, 120, 365 and 371 and any other applicable statutes.

STATEMENT REGARDING FEDERALLY SPONSORED RESEARCH OR DEVELOPMENT

This invention was made with Government support under Grant No. W81XWH-10-1-0519, awarded by the U.S. Army, Medical Research and Materiel Command and Grant No. N66001-11-1-4125, awarded by the U.S. Navy, Office of Navy Research. The Government has certain rights in the invention.

FIELD OF THE INVENTION

The field of the invention generally relates to microfluidic devices. More particularly, the field of the invention relates to microfluidic devices used in solution exchange applications for cell and particle suspensions

BACKGROUND

The current standard technique to transfer particles or cells from one solution to another at the macroscale level involves centrifugation and re-suspension. This is a manual labor and time intensive process that is not easily miniaturized or integrated due to the bulk of the centrifuge machine and manual pipetting steps required. Centrifugation and pipetting steps are, of course, labor and time intensive processing steps. Attempts have been made to miniaturize this capability using microstructures to divert cells while not diverting the fluid component. For example, Morton et al. discloses an asymmetric post array used in pressure-driven microfluidic flow to move particles of interest across multiple, independent chemical streams. See Morton, K. J. et al., Crossing microfluidic streamlines to lyse, label and wash cells, Lab Chip 8, 1448-1453 (2008).

Others have used dielectrophoresis (DEP) to transfer particles electrically. For example, Tronay et al. have used activated DEP electrodes in a microfluidic device where particles can be continuously functionalized in flow. The device uses a particle exchanger which allows for particles to be taken from one medium and exposed to some reagent while minimizing mixing of the two liquids. In the exchanger, two liquids are brought in contact and particles are pushed from one to the other by the application of a dielectrophoretic force. See Tornay, R. et al., Dielectrophoresis-based particle exchanger for the manipulation and surface functionalization of particles, Lab Chip 8, 267-273 (2008). Still others have used acoustic manipulation of suspended particles, in which particles in a laminar flow microchannel are continuously translated from one medium to another with virtually no mixing. See Petersson, F. et al., Carrier Medium Exchange through Ultrasonic Particle Switching in Microfluidic Channels, Anal. Chem. 77, 1216-1221 (2005). Yet another approach uses hydrodynamic filtration in which the virtual width of flow in a microchannel determines the size of filtered cells/particles. See Yamada M. et al., Millisecond treatment of cells using microfluidic devices via two-step carrier medium exchange, Lab Chip, 8, 772-778 (2008).

While some microfluidic-based sorting devices have been proposed for solution exchange, there are concerns about device complexity, and the speed of operation. In many cases, the speed of exchange is rather slow and cannot be integrated, for example, with additional downstream processing applications such as cytometry. Microfluidic-based solution exchange systems should have high-throughput, be easy to multiplex, should be able to position particles or cells for possible downstream interrogation, and should have fast transfer. The prior techniques do not satisfy all of these criteria.

SUMMARY

In one embodiment, a microfluidic system for solution exchange includes a first inlet channel operatively coupled to a source of particles suspended in a fluid and a second inlet channel operatively coupled to an exchange fluid. The system includes a transfer channel having a proximal end and a distal end, the proximal end of the transfer channel connected to the first inlet channel and the second inlet channel. At least one outlet channel is connected to a distal end of the transfer channel. A first pump is configured to pump the source of particles suspended in a fluid at a first flow rate and a second pump is configured to pump the exchange fluid at a second flow rate wherein the ratio of the second flow rate to the first flow rate is at least 1.5.

In another embodiment, a microfluidic system for solution exchange includes a first inlet channel operatively coupled to a source of particles suspended in a fluid and a second inlet channel operatively coupled to an exchange fluid. The system includes a first transfer channel having a proximal end and a distal end, the proximal end of the first transfer channel connected to the first inlet channel and the second inlet channel. At least one outlet channel is connected to a distal end of the first transfer channel. A first pump is configured to pump the source of particles suspended in a fluid at a first flow rate and a second pump configured to pump the exchange fluid at a second flow rate wherein the ratio of the second flow rate to the first flow rate is at least 1.5. The system includes a third inlet channel operatively coupled to the at least one outlet channel and a second transfer channel having a proximal end and a distal end, the proximal end of the second transfer channel connected to the third inlet channel and the at least one outlet channel. A third pump is configured to pump a second exchange fluid into the third inlet channel. At least one outlet channel is connected to a distal end of the second transfer channel.

In another embodiment, a method of exchanging fluids with suspended particles includes providing a microfluidic device comprising a first inlet channel operatively coupled to a source of particles suspended in a fluid and a second inlet channel operatively coupled to an exchange fluid, a transfer channel having a proximal end and a distal end, the proximal end of the transfer channel connected to the first inlet channel and the second inlet channel, and first and second outlet channels connected to a distal end of the transfer channel. The source of particles suspended in a fluid is flowed at a first flow rate into the first inlet channel. The exchange fluid is flowed at a second flow rate into the second inlet channel wherein the ratio of the second flow rate to the first flow rate is at least 1.5. Particles are collected in one of the first and second outlet channels. Fluid substantially free of particles is collected in the other of the first and second outlet channels.

BRIEF DESCRIPTION OF THE DRAWINGS

FIGS. 2A-2D are high speed photographic images taken of a transfer channel 36 that includes co-flow of a fluid containing a particle 14 (a 19 μm microsphere) as well as a dye fluid (darker, lower fluid).

FIG. 3A illustrates a top view of an alternative embodiment of a microfluidic system that incorporates downstream analysis.

FIG. 3B illustrates a side cross-sectional view of the embodiment of FIG. 3A taken along the line B-B'.

FIG. 3C illustrates a side cross-sectional view of the embodiment of FIG. 3A taken along the line C-C'.

FIG. 3D illustrates a side cross-sectional view of the embodiment of FIG. 3A taken along the line D-D'.

DETAILED DESCRIPTION OF THE ILLUSTRATED EMBODIMENTS

Figure 1:
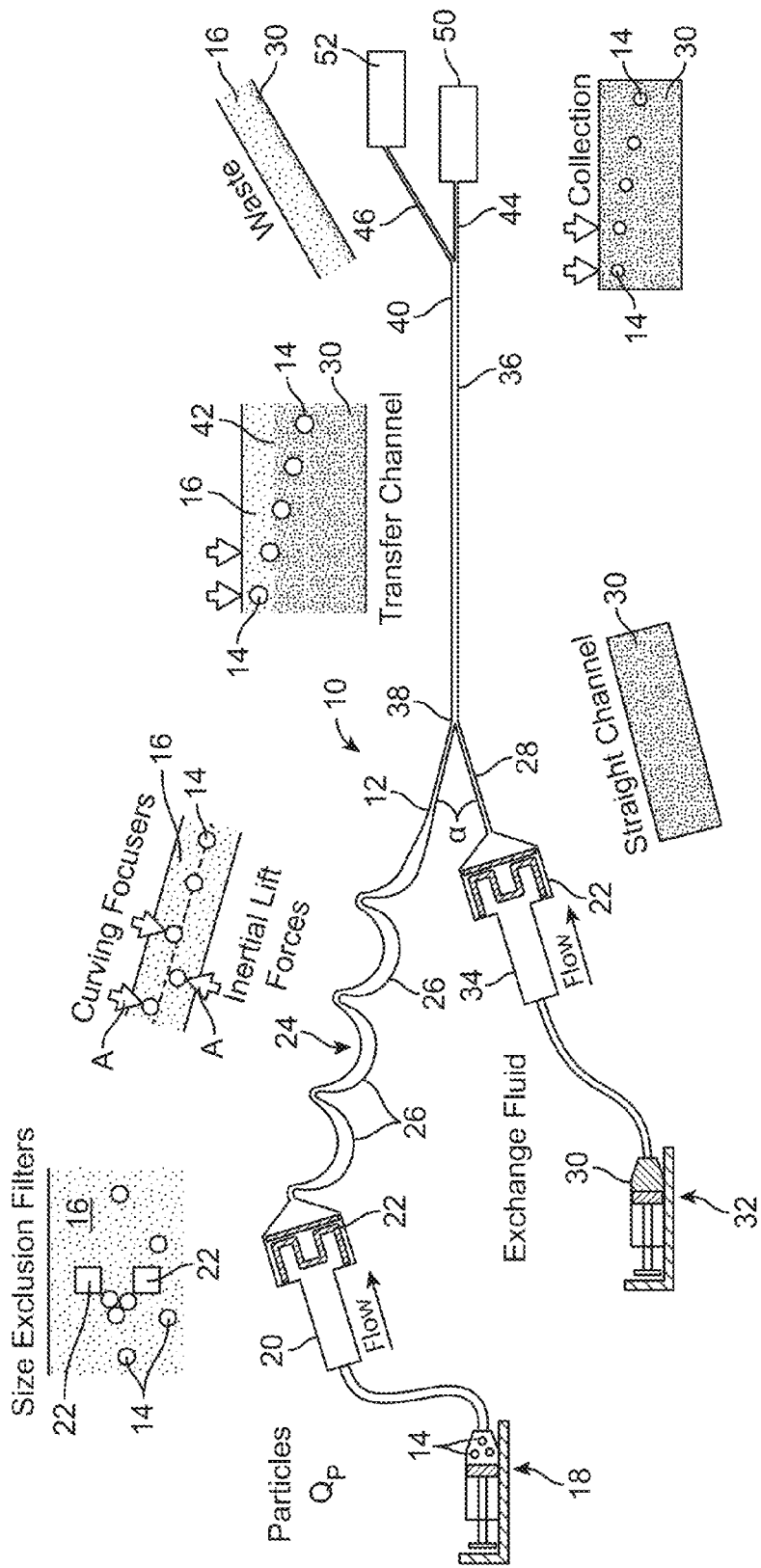
FIG. 1 illustrates a microfluidic system according to one embodiment.

FIG. 1 illustrates a microfluidic system 10 for solution exchange according to one embodiment. The microfluidic system 10 includes a first inlet channel 12 that is operatively coupled to source of particles 14 suspended in a fluid 16. The term "particle," as used herein, is meant to refer broadly to objects capable of being suspended in fluid 16. Exemplary particles include such things as beads, cells, vesicles, micelles, and the like. The particles 14 and the fluid 16 are flowed into the first inlet channel 12 using a pump 18 such as a syringe pump as illustrated in FIG. 1 although other pumping devices may be used. The pump 18 interfaces with first inlet channel 12 at an inlet 20. The inlet 20 may include optional filters 22 downstream thereof which may be structures dimensioned (e.g., posts, fins, or the like) to trap large debris and aggregates while allowing passage of particles 14.

Still referring to FIG. 1, the first inlet channel 12 may have a width within the range of about 50 μm to about 100 μm and a height within the range of about 20 μm to about 30 μm although other dimensions may be used. The first inlet channel 12 may include an optional focusing region 24. The focusing region 24 may be used to focus the particles 14 laterally and/or longitudinally within the first inlet channel 12. In one aspect, the focusing region 24 includes a plurality of curves 26 which may be symmetrically or asymmetrically shaped to promote focusing. Arrows A in FIG. 1 illustrate inertial forces within the curves 26 that focus the particles 14. Examples of such focusing structures may be found, for example, in the publication by DiCarlo et al., Continuous inertial focusing, ordering, and separation of particles in microchannels, Proc. Natl. Acad. Sci. 104(48): 18892-18897 (2007), which is incorporated by reference herein. Another type of focusing region 24 may be found in U.S. Pat. No. 8,361,415, which is also incorporated by reference herein. In still another option, the first inlet channel 12 may be lengthened because a longer length microchannel tends to focus particles 14 therein.

Still referring to FIG. 1, the microfluidic system 10 includes a second inlet channel 28 that is operatively coupled to an exchange fluid 30. The exchange fluid 30 may include any number of fluids. For example, the exchange fluid 30 may include a wash such as phosphate buffered saline (PBS). The exchange fluid 30 may also include a reagent or the like therein. For example, the exchange fluid 30 may include a dye or label therein. The exchange fluid 30 is flowed into the second inlet channel 28 using a pump 32 such as a syringe pump as illustrated in FIG. 1 although other pumping devices may be used. The pump 32 interfaces with second inlet channel 28 at an inlet 34. The inlet 34 may include optional filters 22 located downstream thereof the same as or similar to those described in the context of the first inlet channel 12. The second inlet channel 28 may have a width within the range of about 50 μm to about 100 μm and a height within the range of about 20 μm to about 30 μm although other dimensions may be used. The length of the second inlet channel 28 may vary but is typically a few millimeters (e.g., 2 mm)

Still referring to FIG. 1, both the first inlet channel 12 and the second inlet channel 28 are connected to a downstream transfer channel 36. The transfer channel 36 has a proximal end 38 and a distal end 40 with the first inlet channel 12 and the second inlet channel 28 intersecting with the proximal end 38 of the transfer channel 36. Both the first inlet channel 12 and the second inlet channel 28 are angled relative to the transfer channel 36. Preferably, the first inlet channel 12 and the second inlet channel 28 are symmetrically angled relative to the transfer channel 36. For example, both the first inlet channel 12 and the second inlet channel 28 may be angled (α) approximately at or less than 60° relative to each other. The transfer channel 36 typically has a height that is the same as the height of the first inlet channel 12 and the second inlet channel 28 however, in multiplexed embodiments it is possible to have multi-planar structures in which case the height does not have to be equal to that of the first inlet channel 12 and the second inlet channel 28. The width of the transfer channel 36 is generally roughly equal to the summation of the respective widths of the first inlet channel 12 and the second inlet channel 28. For example, widths of the transfer channel 36 typically fall within the range of about 75 μm to about 100 μm. Generally, the cross-sectional aspect ratio of the height to width (H:W) is less than 1 and preferably less than ⅔ (e.g., 0.5). The length of the transfer channel 36 is typically greater than or equal to about 1 cm although other lengths may be used.

In one aspect of the invention, the flow rate at which the particles 14 suspended in the fluid 16 are flowed into the first inlet channel 12 is different than the flow rate at which the exchange fluid 30 is flowed into the second inlet channel 28. In this regard, the exchange fluid 30 should be flowed into the second inlet channel 28 at a flow rate that exceeds the flow rate of the particles 14 suspended in fluid 16. More particularly, it has been found that the ratio of the flow rate of the exchange fluid 30 to the flow rate of the particles 14 suspended in fluid 16 should be at least about 1.5. In another aspect of the invention, the ratio is within the range of about 1.5 to about 2.0. Typically, the flow rate for the particles 14 suspended in fluid 16 may be in the range of about 50 µl/min. to about 80 µl/min. The flow rate for the exchange fluid 30 may be in the range of about 90 µl/min. to about 120 µl/min although flow rates outside this range may also be used. Generally, the microfluidic device 10 should be constructed such that a Particle Reynolds Number ($R_p$) is between the range of about 0.25 to about 1.87. $R_p$ is defined as follows:

$$R_p = \rho U \alpha^2 / \mu H \quad \text{(Eq. 1)}$$

where ρ is the density, U is the maximum channel velocity, α is the particle diameter, µ is the viscosity, and H is the channel height. Moreover, the Reynolds number of the fluid flowing through the first inlet channel 12 and the second inlet channel 28 should be less than about 2,000 so as to maintain laminar and not turbulent flow.

The flow rate is high such that an interface 42 is formed between the fluid 16 containing the particles 14 and the exchange fluid 30. This interface 42 is advantageously maintained along substantially the entire length of the transfer channel 36. In this regard, a co-flow state is maintained between the exchange fluid 30 and the fluid 16 containing the particles 14 which is maintained throughout the length of the transfer channel 36. Maintenance of this interface 42 and the establishment of the co-flow state means that there is very little diffusion across this interface. The Peclet number (ratio of convection to diffusion) is typically high (e.g., ~160,000) such that diffusion across the interface 42 is negligible. Of course, the invention is not limited to a particular Peclet number.

Still referring to FIG. 1, the microfluidic system 10 includes a plurality of outlet channels 44, 46. While two such outlet channels are illustrated in FIG. 1, in other embodiments there may be more outlet channels. The outlet channels 44, 46 have dimensions to alter their respective fluidic resistance values. In some embodiments, the outlet channels 44, 46 may have the same height as the upstream transfer channel 36 but different widths so as to adjust the rate of fluid volume which passes through each outlet channel 44, 46. In the embodiment of FIG. 1, the particles 14 first enter the transfer channel 36 containing with carrier fluid 16. The particles 14 feel inertial lift forces indicated by arrows A that push the particles 14 toward an equilibrium position ($X_{eq}$) that generally lies within the center region of the transfer channel 36 (centerline is shown by dashed line 48). However, because the flow rate of the exchange fluid 30 is higher than the flow rate of the fluid 16 with suspended particles 14, more than half of the transfer channel 36 is filled with exchange fluid 30. This can be seen in cross-sectional view of the transfer channel 36 in FIG. 1 where the level of exchange fluid 30 is above the centerline 48.

As stated above, the equilibrium position ($X_{eq}$) in the transfer channel 36 lies within the exchange fluid 30. Particles 14 are thus pushed by inertial lift forces from the suspension fluid 16 of the co-flow and into the exchange fluid 30 of the co-flow. The particles 14 after reaching the equilibrium position ($X_{eq}$) are completely within the exchange fluid 30. The particles 14 are thus exchanged from the original suspension fluid 16 to the exchange fluid 30. The particles 14 continue to travel downstream toward the junction of the plurality of outlet channels 44, 46. In the embodiment of FIG. 1, the particles 14 exit the transfer channel 36 and enter outlet channel 44. The other outlet channel 46 which is angled relative to the transfer channel 36 collects the original fluid 16 used for suspension of the particles 14 along with some of the exchange fluid 30. Substantially all or all of the particles 14 however will be collected in outlet channel 44. In this embodiment, outlet channel 44 collects the particles 14 and exchange fluid 30 while the other outlet channel 46 contains no particles 14 but a combination of the original fluid 16 plus some collection fluid 30. In this regard, outlet channel 46 contains fluid that is substantially free of particles 14. The ratio of fluid resistance of the two outlet channels 44, 46 is adjusted either through the geometric construction of the channels 44, 46 or through some sort of application of pressure (either positive or negative). For example, in the microfluidic system 10 of FIG. 1 it has been found that a ratio of fluid resistance of around 2.6 (resistance of outlet channel 46: outlet channel 44) although this number varies depending on the orientation of the outlets 44, 46 as well as the total number of outlets.

FIGS. 2A-2D are high speed photographic images taken of a transfer channel 36 that includes co-flow of a fluid containing a particle 14 (a 19 µm microsphere) as well as a dye fluid (darker, lower fluid). FIG. 2A illustrates the particle 14 at the initial time (t=0.00 ms) whereby the particle is entering the transfer channel 36 from the first inlet channel 12. FIG. 2B illustrates the particle 14 being subject to the inertial lift forces ($F_L$) at a time of 0.51 ms. The particle 14 is beginning to move toward the equilibrium position ($X_{eq}$). FIG. 2C illustrates the same particle 14 at a time of 1.50 ms whereby the particle 14 is continuing the migration into the dye. FIG. 2D illustrates the particle 14 at the equilibrium position ($X_{eq}$) which completely lies within the dye solution.

The outlet channels 44, 46 are coupled to respective outlet chambers 50, 52 in FIG. 1 where the particles 14 and fluids are then contained (e.g., waste in chamber 52). Alternatively, one or more of the outlet channels 44, 46 may interface with additional microfluidics or devices for subsequent processing and/or analysis. For example, FIG. 3 illustrates one such embodiment of a microfluidic system 10 that incorporates downstream analysis. FIGS. 3A-3D illustrate a similar embodiment as that illustrated in FIG. 1 with one difference being the presence of three (3) outlet channels 54, 56, 58. In this embodiment, as best seen in FIG. 3A, the particles 14 are cells and the fluid 16 contains fluorescent probes 60. The first inlet channel 12 is flowed at a flow rate of 60 µL/minute while the second inlet channel 28 is flowed with a wash solution 30 such as PBS at a rate of 90 µL/minute (other flow rates could also be used). As seen in FIG. 3B, the cells 14 are initially within the fluid 16 that contains the fluorescent probes 60. The cells 14 migrate out of the probe-containing stream of the co-flow and into the PBS exchange solution 30 within the transfer channel 36. This is seen in FIG. 3C which illustrates a cross-sectional view of the transfer channel 36. At the outlet junction, cells 14 contained within the PBS exchange solution 30 flow into outlet channel 56 while outlet channels 54, 58 collect, respectively, probe solution 16 and PBS exchange solution 30 as seen in FIG. 3D. The outlet channel 56 continues on to analyzer 62. The analyzer 62 may include any number of analysis devices such as a flow cytometer, fluorescent-activated cell sorter (FACS), and imager. For example, in the embodiment of FIGS. 3A-3D, the analyzer 62 may comprise a fluorescent detection device that detects fluorescent cells 14 through laser interrogation.

One benefit of the microfluidic system 10 described herein is that cells 14 can quickly be interrogated. In the embodiment of FIGS. 3A-3D, for example, the fluorescent probe 60 may have weak binding affinity to the cell 14 and after binding quickly disassociates with the underlying cell 14. With this microfluidic system 10, the quick exchange of the solution as well as the rapid downstream analysis permits interrogation before the fluorescent probe 60 disassociates with the cell 14. Cells 14 are flow directly into the analyzer 62 without any time-consuming wash steps being needed. Further, the signal-to-noise ratio is improved by eliminating background fluorophores via outlet channel 54. While flow cytometry can usually discriminate between free and bound fluorescent probes, the study of low affinity interactions requires higher concentrations of free probes which hinder the accuracy of the flow cytometer in this task. With this microfluidic system 10 probe-bound objects can be transferred to a new solution with low background, and with the implementation of a fluorescence detection system, immediately record fluorescence measurements.

Figure 4:
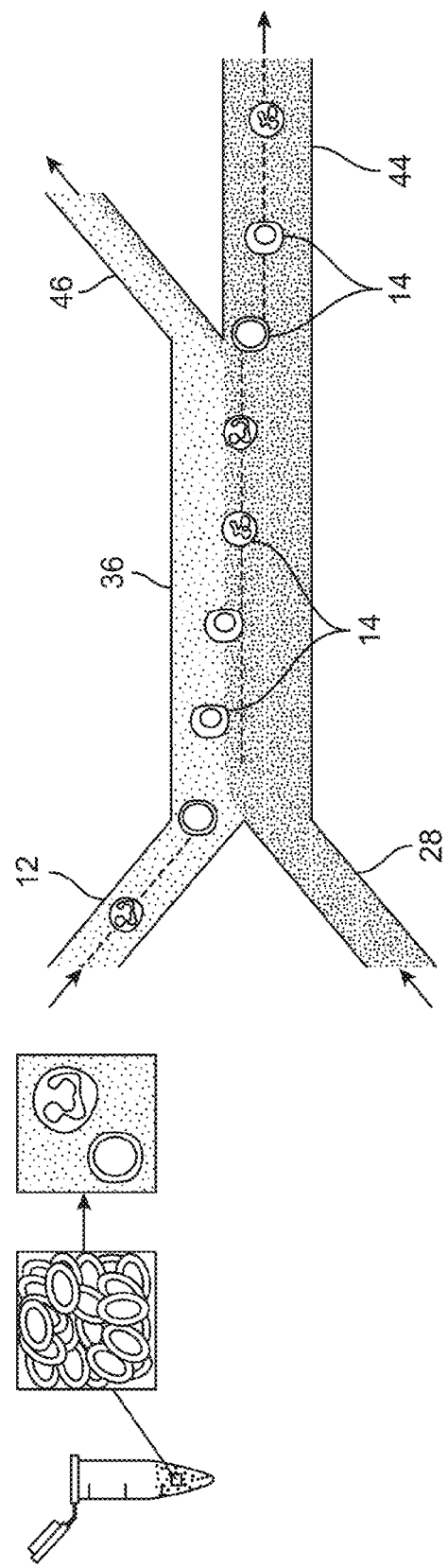
FIG. 4 illustrates a microfluidic system according to another embodiment.

The microfluidic system 10 may be used for many different applications. One primary application of the rapid solution exchange approach disclosed herein is sample preparation. The primary tasks in sample preparation include labeling of cells with targets such as antibodies which are then washed to remove un-bound antibodies. For example, cells could be incubated with antibody then run through the microfluidic system 10 which then transfers labeled cells to a clean solution. These cells could then be analyzed using an inline fluorescence detection system such as that illustrated in FIG. 3A whereby fluorescence measurements can be immediately obtained. Alternatively, the cells could be analyzed offline. Another application of the device is in the sample preparation involving blood. When working with blood, it is typically important to remove the red blood cells (RBCs). RBC removal is accomplished by hypotonic lysis. One use of the microfluidic system 10 is mixing whole blood containing RBCs with lysis buffer and fluorescent label targeted to white blood cells. FIG. 4 illustrates an example of the microfluidic system 10 being used in this manner.

As seen in FIG. 4, the solution contained lysed RBCs (i.e., ghosts), hemoglobin, and nucleic acid stains (targeting white blood cells and incubated for 10 minutes) were injected into the first inlet channel 12 at a rate of 60 µL/min. A PBS solution was flowed in the second inlet channel 28 at a rate of 120 µL/min. The RBC ghosts and hemoglobin establish one part of the co-flow within the transfer channel 36 while the PBS solution establishes the remaining portion (lower portion in FIG. 4) of the co-flow in the transfer channel 36. The white blood cells 14, with stained nuclei, then migrate due to inertial forces into the PBS solution. The entrained white blood cells then exit via a first outlet 44 while the RBC debris and hemoglobin leave via second outlet 46. Table 1 below illustrates the measured relative background fluorescence per 100 µm$^2$.

TABLE 1

| Channel | Relative background fluorescence per 100 µm$^2$ |
|---|---|
| Inlet | 1.00 |
| Reject (RBCs) | 0.89 |
| Collect (WBCs) | 0.30 |

Figure 5:
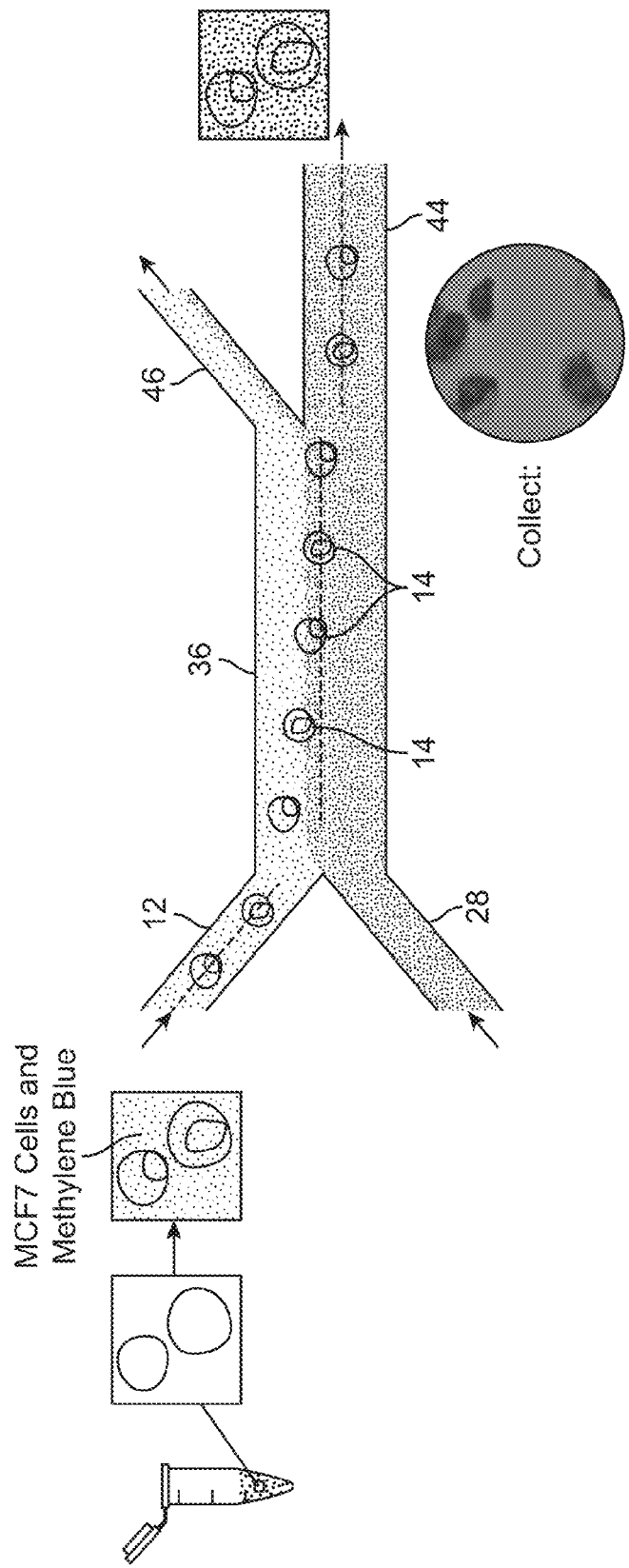
FIG. 5 illustrates a microfluidic system according to another embodiment that is can be used in histological staining applications.

The microfluidic system 10 can also be used in histological staining applications as illustrated in FIG. 5. Here a microfluidic system 10 similar to that disclosed in FIG. 1 is used in connection with the staining of cells 14. In this example, MCF7 cells were mixed with a stain (Methylene Blue) and flowed into the first inlet channel at a rate of 60 µL/min. A PBS solution was flowed in the second inlet channel 28 at a rate of 110 µL/min. The stained cells migrated to the "clean" PBS portion of the co-flow while the stain remained in the remaining portion of the co-flow. The entrained stained cells then exit via a first outlet 44 while the stain and other non-cell material leave via second outlet 46. In this example, the first outlet 44 captures 96% of the cells.

Figure 6:
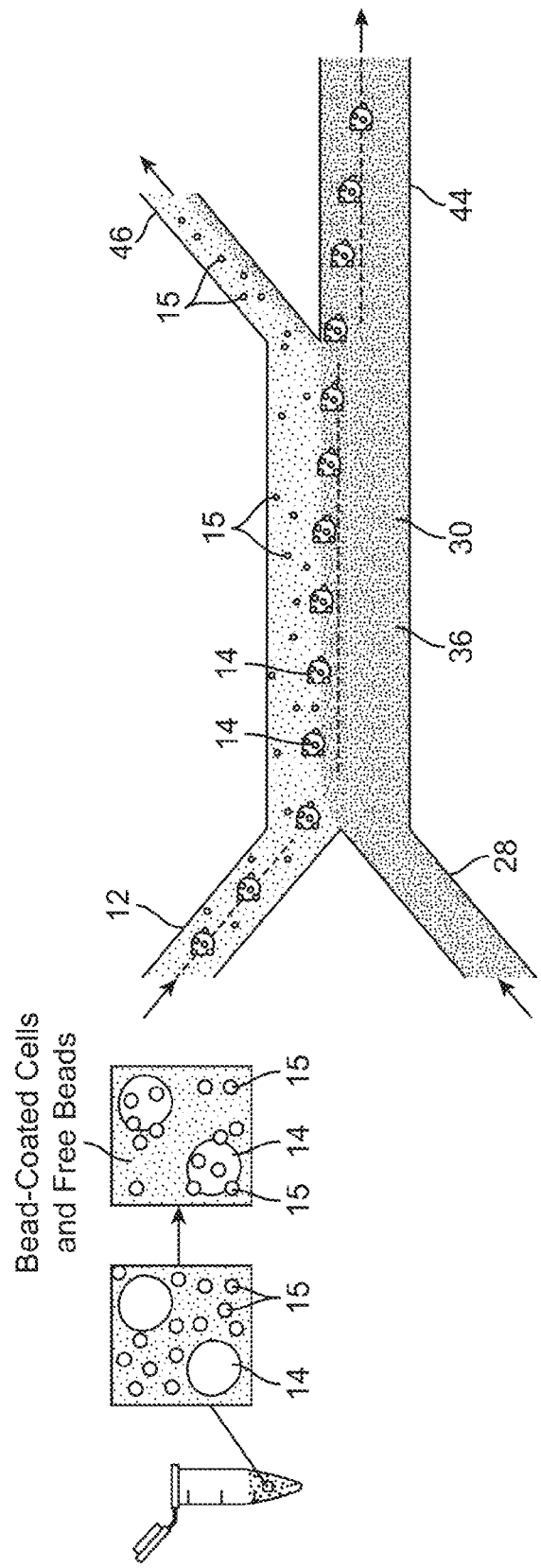
FIG. 6 illustrates a microfluidic system according to another embodiment.

FIG. 6 illustrates still another application of the microfluidic system 10. In this embodiment, particles that are cells 14 are mixed with beads 15 with binding affinity to cells 14 (e.g., functionalized beads or magnetic beads) some of which coat the exterior of the cells 14. The cells 14 along with the beads 15 are flowed into the first inlet channel 12. A PBS or other "clean" solution was flowed in the second inlet channel 28. The cells 14 having beads 15 bound thereto migrated to the "clean" PBS exchange solution 30 portion of the co-flow while the free beads 15 remain in the remaining portion of the co-flow. The bead-laden cells 14 then exit via a first outlet 44 while the free beads 15 leave via second outlet 46.

Another application of the microfluidic device 2 is that particles 14 may be used in conjunction with solution exchange to sequester or elute targets of interest. For example, particles 14 with sizes such that they are subject the same to inertial forces (e.g., the size of cells) may have surfaces functionalized that bind to molecules of interest (e.g., targets). The particles 14 can then be used to bind with the target species and collected while the unwanted molecules can be removed via a waste stream. The reverse could also be employed. For example, previously washed particles 14 having bound targets thereon could be brought into a solution where the molecules elute from the particles 14. The particles 14 could then be captured in a "waste" stream while the other outlet channel(s) can be used to collect the eluted molecules.

One of the advantages of the microfluidic system 10 is that solution exchange happens very quickly (e.g., a couple milliseconds). This allows one to measure dynamic events as they occur in the millisecond time scale. If one had to do this with pipetting or a slow microfluidic method only events in the second or minute time scale would be accessible. Further, the contents of the solutions are not the only important factors. One could have two solutions with different pH or temperatures. These solutions could be used to elute bound molecules, as mentioned above, test the response of materials to these conditions, or bring biosamples into a temperature required for a specific event to occur, like nucleic acid denaturation, annealing, or amplification.

Figure 7:
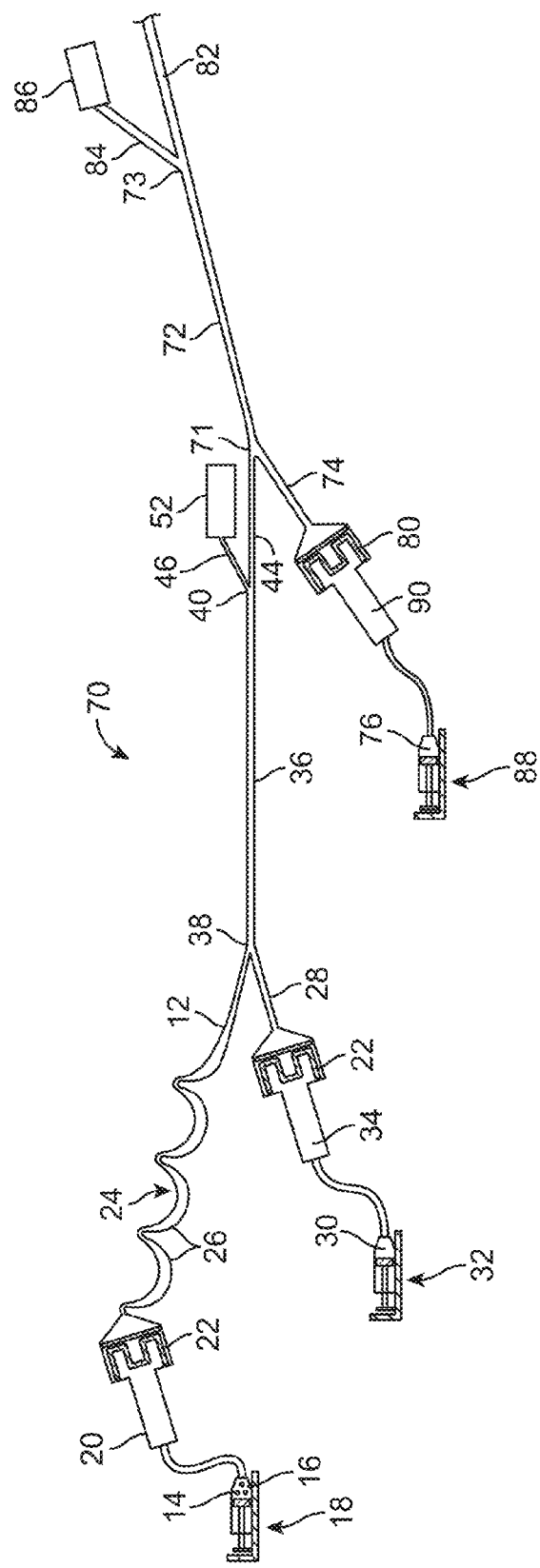
FIG. 7 illustrates a microfluidic system according to another embodiment.

FIG. 7 illustrates another embodiment of a microfluidic system 70. This embodiment includes a two-stage exchange system. The first stage of the microfluidic system 70 is equivalent to that described with respect to FIG. 1 and similar features are labeled with the same reference numbers and will not be described again for clarity purposes. In this embodiment, the outlet channel 44 that contains the particles 14 acts as an "input" channel to another stage of solution exchange. In this regard, the outlet channel 44 intersects with a second transfer channel 72. A third inlet channel 74 is provided through which a second exchange fluid 76 is flowed. This second exchange fluid 76 may be the same as or different from the first exchange fluid 30. The third inlet channel 74 is coupled to a pump 88 or the like that is used to deliver the second exchange fluid 76. This may include a syringe pump as is shown in FIG. 7 although other pumping devices may be used. The pump 88 interfaces with an inlet 90 that may have optional filters 80 (like filters 22) to exclude debris and the like.

The second transfer channel 72 has a proximal end 71 that starts at the junction of the outlet channel 44 and the third inlet channel 74 and a distal end 73 that terminates at third outlet channel 82 and fourth outlet channel 84. The particles 14 that enter the second transfer channel 72 from the outlet 44 migrate in a similar manner as described herein to the second exchange fluid 76. The particles 14 remain therein and travel downstream to the third outlet channel 82 while non-particulate matter (e.g., debris, impurities) can then be shunted to the fourth outlet channel 84 and into chamber 86. In this embodiment, there is double-solution exchange in a very short period of time. For example, as one example, the first stage of solution exchange (with exchange fluid 30) may include a wash or clean-up while the second stage of solution exchange (with second exchange fluid 76) may include a lysing agent. In this example, the nucleus may then be collected in one of the downstream collection channels 82, 84. As another example, the first stage of solution exchange (with exchange fluid 30) may include a wash or clean-up while the second stage of solution exchange (with second exchange fluid 76) may include a dye. This embodiment is particularly suited for sample preparation where multiple steps are used. Not only can the microfluidic device 10, 70 be used for immunohistochemistry or selective lysis, it can also be used for transfection, fixation, and permeabilization.

Figure 8A:
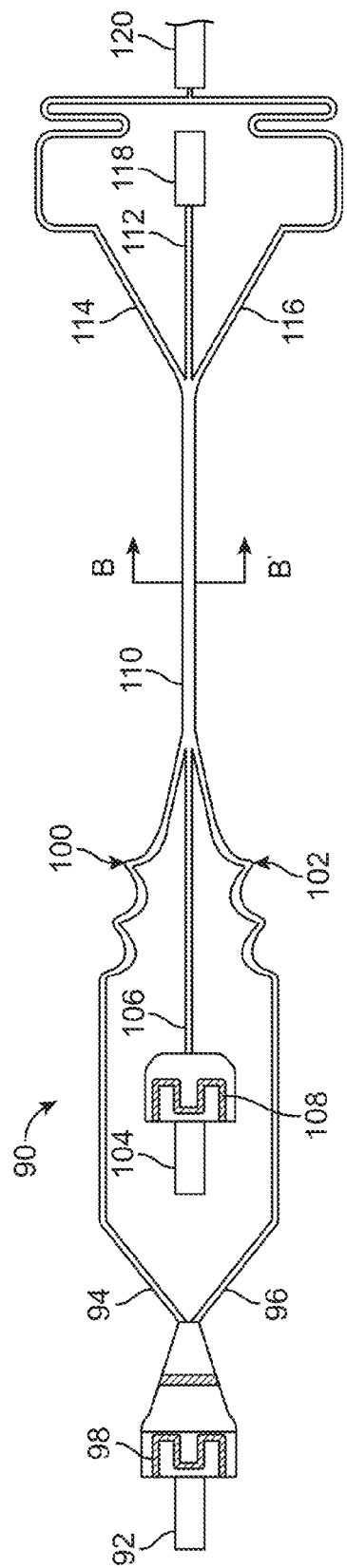
FIG. 8A illustrates a microfluidic system according to another embodiment.

FIG. 8A illustrates another embodiment of a microfluidic system 90. This system 90 includes a first inlet 92 that is connected to a first inlet channel 94 and second inlet channel 96 that bifurcate from the common first inlet 92. The first inlet 92 is operatively coupled to a source of particles contained in a fluid (now shown) that is similar to the other embodiments described herein. Namely, the first inlet 92 is connected to a pump (not shown) such as a syringe pump or the like that is configured to flow particles suspended in solution through the first inlet 92 and into the first and second inlet channels 94, 96. The first inlet 92 may include filters 98 downstream thereof which may be structures dimensioned (e.g., posts, fins, or the like) to trap large debris and aggregates while allowing passage of particles. As seen in FIG. 8A, the first and second inlet channels 94, 96 are connected respectively, to optional focusing regions 100, 102 which may comprise a plurality of microfluidic curves as previously discussed herein.

The microfluidic system 90 includes a second inlet 104 that is connected an inlet channel 106. The second inlet 104 is operatively coupled to an exchange fluid (not shown) that is similar to the other embodiments described herein. Namely, the second inlet 104 is connected to a pump such as a syringe pump or the like that is configured to exchange fluid through the second inlet 104 and into the inlet channel 106. The second inlet 104 may include filters 108 downstream thereof which trap large debris and aggregates similar to those described with respect to other filters. The focusing regions 100, 102 intersect with the inlet channel 106 at the beginning of transfer channel 110. Transfer channel 110 extends for at least 1 cm and terminates at three outlet channels 112, 114, 116. There is a central outlet channel 112 that is configured to collect particles in the exchange solution. The two outer outlet channels 114, 116 are configured to collect waste solution (e.g., fluid suspending particles). The central outlet channel 112 may be coupled to a collection chamber 118 or, alternatively, the central outlet channel 112 may continue onward to additional downstream processing such as an analyzer as described herein.

The two outer outlet channels 114, 116 may be connected to a common collection chamber 120 as is illustrated in FIG. 8A.

Figure 8B:
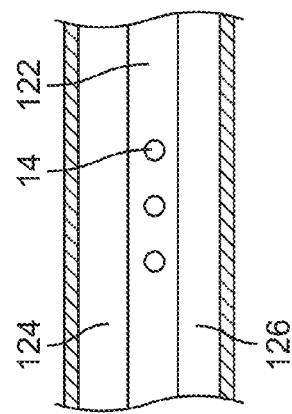
FIG. 8B illustrates a cross-sectional view of the transfer channel taken along the line B-B' of FIG. 8A.

FIG. 8B illustrates a cross-sectional view (taken along line B-B' of FIG. 8A) of the fluid layers created within the transfer channel 110 of the microfluidic system 90 of FIG. 8A. As seen in FIG. 8B, there are three distinct layers of fluid created including a center layer 122 of fluid includes the exchange fluid that is flowed into the microfluidic system 90 via the second inlet 104 as well as two outer layers 124, 126. Particles 14 have migrated from the two outer layers 124, 126 into the center layer 122 to reach an equilibrium position ($X_{eq}$). The two outer layers 124, 126 contain particle suspension fluid, namely, the fluid being delivered into the microfluidic system 90 via the first inlet 92. This fluid, along with any debris or other material, is transferred to the two outer outlet channels 114, 116.

The microfluidic systems 10, 70, 90 may be manufactured using processes commonly known to those skilled in the art to make microfluidic devices. For example, the microfluidic system 10, 70, 90 may be designed using software such as AutoCAD (Autodesk, San Rafael, Calif., USA). Transparency photomasks for these designs can be printed at 20,000 dots per inch (CAD/Art Services, Inc., Bandon, Oreg., USA). Molds for replica molding can then be prepared using these masks. Negative photoresist, SU-8 50 (MicroChem, Newton, Mass., USA) is spun on a four (4) inch Silicon wafer at 4,000 rotations per minute. The coated wafer is then soft baked at 65° C. for 5 minutes then 95° C. for 15 minutes. The wafer is then exposed under near UV at 8.0 mW/cm$^2$ for 30 seconds. A post-exposure bake of the wafer can be carried out at 65° C. for 2 minutes then at 95° C. for 3.5 minutes. The unexposed photoresist is then developed in SU-8 Developer (MicroChem) until an isopropyl alcohol rinse produced no white film. The height of the resulting features can be characterized by a surface profiler.

The width of microchannels immediately before and after the extensional flow region was 67 μm. The height of the features in the device was 28 μm. The mold is then taped to the lower plate of a petri dish with features facing up and an approximately 6 mm layer of Sylgard 184 Silicone Elastomer (Dow Corning, Midland, Mich., USA), polydimethylsiloxane (PDMS), mixed 10 parts base to 1 part curing agent, is poured on top. The cast mold is then placed in a vacuum chamber and the chamber was evacuated for 30 minutes to remove air from the curing polymer. It was then moved to an oven set to 65° C. for 3 hours. The devices were cut from the mold and inlet and outlets were punched into the cured polymer. They were then placed in a plasma cleaner along with slide glasses to be activated. After a 30 second exposure to air plasma the activated surfaces of PDMS and glass were placed in contact to form permanent covalent bonds between the two materials. While a PDMS-based construction is described herein it should be understood that the system and methods disclosed herein are not so limited. Other microfluidic manufacturing methods may be employed.

The microfluidic systems 10, 70, 90 discussed herein offer the ability for high-throughput processing of particles 14 for solution exchange. For example, the microfluidic systems 10, 70, 90 are able to achieve throughputs in excess of 1,000 particles 14 per second. Further, various aspects of the different embodiments described herein may be substituted with one another. As an example, the downstream analyzer 62 may be used with any of the embodiments described herein. Thus, while several embodiments have been described herein it should be appreciated that various aspects or elements are interchangeable with other separate embodiments.

While embodiments have been shown and described, various modifications may be made without departing from the scope of the inventive concepts disclosed herein. The invention(s), therefore, should not be limited, except to the following claims, and their equivalents.

What is claimed is:

1. A method of exchanging fluids with suspended particles comprising:
   providing a microfluidic device comprising a first inlet channel operatively coupled to a source of particles suspended in a fluid; a second inlet channel operatively coupled to an exchange fluid; a linear and longitudinally symmetrical transfer channel having a proximal end and a distal end, the proximal end of the transfer channel connected to the first inlet channel and the second inlet channel; and first and second outlet channels connected to a distal end of the transfer channel;
   flowing the source of particles suspended in a fluid at a first flow rate into the first inlet channel;
   flowing the exchange fluid at a second flow rate into the second inlet channel wherein the ratio of the second flow rate to the first flow rate is at least 1.5;
   equilibrating the particles from the source of particles suspended in the fluid at an equilibrium position ($X_{eq}$) located within the transfer channel, the equilibrium position ($X_{eq}$) contained within the exchange fluid, wherein inertial lift forces in the transfer channel direct the particles from the source of particles to the equilibrium position ($X_{eq}$) within a center region of the transfer channel;
   collecting the equilibrated particles in the first outlet channel; and
   collecting fluid substantially free of the equilibrated particles in the second outlet channel.

2. The method of claim 1, wherein the source of particles suspended in the fluid comprise cells.

3. The method of claim 2, wherein the source of particles suspended in the fluid comprise cells and functionalized beads that bind to the cells.

4. The method of claim 1, wherein the exchange fluid comprises a wash fluid.

5. The method of claim 1, wherein the exchange fluid comprises a dye.

6. The method of claim 1, further comprising analyzing the particles collected in the first outlet channel with an analyzer selected from the group consisting of a flow cytometer, fluorescent-activated cell sorter (FACS), and imager.

7. The method of claim 1, wherein the microfluidic device further comprises a third inlet channel operatively coupled to the first outlet channel and a second linear and longitudinally symmetrical transfer channel having a proximal end and a distal end, the proximal end of the second transfer channel connected to the third inlet channel and the first outlet channel wherein third and fourth outlet channels connect to a distal end of the second transfer channel;
   flowing a second exchange fluid into the third inlet channel;
   equilibrating the particles at an equilibrium position ($X_{eq}$) located within the second transfer channel, the equilibrium position ($X_{eq}$) contained within the second exchange fluid;
   collecting the equilibrated particles in one of the third and fourth outlet channels; and
   collecting fluid substantially free of the equilibrated particles in the other of the third and fourth outlet channels.

8. The method of claim 7, wherein a flow rate of the second exchange fluid is at least 1.5 times a flow rate of fluid through the first outlet channel connected to a distal end of the first transfer channel.

9. The method of claim 1, wherein the ratio of the second flow rate to the first flow rate is between about 1.5 and about 2.0.

10. The method of claim 1, wherein the exchange fluid comprises a reagent.

11. The method of claim 1, wherein the source of particles suspended in the fluid flowed in the first inlet channel comprise particles bound with a target and wherein the second outlet channel comprises unbound targets in a fluid that is substantially free of particles.

12. The method of claim 1, wherein the source of particles suspended in the fluid further comprises a fluorescent probe and the exchange fluid comprises a wash solution.

13. The method of claim 1, further comprising fluorescently interrogating the particles collected in the first outlet channel.

14. The method of claim 1, wherein the source of particles suspended in the fluid comprises blood and a nucleic acid stain.

15. The method of claim 1, wherein the transfer channel comprises an aspect ratio (height/width) that is <1 and wherein the center region of the transfer channel is located along a center of the width.

* * * * *